(12) United States Patent
Michaud

(10) Patent No.: US 11,519,891 B2
(45) Date of Patent: Dec. 6, 2022

(54) TECHNIQUES FOR PROVIDING DATA ACQUISITION INTERFACES FOR ANALYTICAL INSTRUMENTS

(71) Applicant: WATERS TECHNOLOGIES IRELAND LIMITED, Dublin (IE)

(72) Inventor: Andrew Michaud, Bellingham, MA (US)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 244 days.

(21) Appl. No.: 16/865,844

(22) Filed: May 4, 2020

(65) Prior Publication Data

US 2020/0348273 A1 Nov. 5, 2020

Related U.S. Application Data

(60) Provisional application No. 62/842,168, filed on May 2, 2019.

(51) Int. Cl.

| | |
|---|---|
| *G01N 30/86* | (2006.01) |
| *G01N 27/622* | (2021.01) |
| *G05B 15/02* | (2006.01) |
| *H01J 49/00* | (2006.01) |
| *G01N 30/02* | (2006.01) |

(52) U.S. Cl.
CPC ........... *G01N 30/86* (2013.01); *G01N 27/622* (2013.01); *G05B 15/02* (2013.01); *H01J 49/0036* (2013.01); *G01N 2030/025* (2013.01); *G01N 2030/027* (2013.01)

(58) Field of Classification Search
CPC .............. G01N 30/86; G01N 27/622; G01N 2030/025; G01N 2030/027; G05B 15/02; H01J 49/0036; G16H 40/63; G16H 10/40
See application file for complete search history.

(56) References Cited

U.S. PATENT DOCUMENTS 5,050,088 A * 9/1991 Buckler ........... G05B 19/41835
  700/96
5,481,707 A * 1/1996 Murphy, Jr. .......... G06F 13/124
  714/48

(Continued)

FOREIGN PATENT DOCUMENTS

CA         2604244 A1    10/2006
WO  WO 2006/108263 A1 * 10/2006  ....... G01N 35/00871

OTHER PUBLICATIONS

International Search Report and Written Opinion for International Application No. PCT/IB2020/054222, dated Jul. 9, 2020, 11 pages.

*Primary Examiner* — Tung S Lau
(74) *Attorney, Agent, or Firm* — Goodwin Procter LLP

(57) ABSTRACT

Techniques and apparatus for executing jobs for performing analytical methods are described. In one embodiment, for example, an apparatus may include at least one memory, and logic coupled to the at least one memory. The logic may be configured to receive a job request from a data system to perform a job, and determine an acquisition system to perform the job, the acquisition system to determine at least one task for the job, provide the at least one task to a task sequencer to coordinate performance of the at least one task, and provide data artifacts to the data system resulting from performance of the at least one task. Other embodiments are described.

20 Claims, 9 Drawing Sheets

(56) References Cited

U.S. PATENT DOCUMENTS

| | | | | |
|---|---|---|---|---|
| 5,596,750 | A * | 1/1997 | Li | G06F 9/466 707/999.107 |
| 7,093,259 | B2 * | 8/2006 | Pulsipher | G06F 11/0787 709/201 |
| 7,159,217 | B2 * | 1/2007 | Pulsipher | G06F 9/4881 718/100 |
| 9,239,996 | B2 * | 1/2016 | Moorthi | G06F 9/5061 |
| 2006/0235690 | A1 * | 10/2006 | Tomasic | G06F 3/0481 704/200 |
| 2009/0204470 | A1 * | 8/2009 | Weyl | G06Q 10/06 705/7.13 |
| 2011/0046910 | A1 * | 2/2011 | Haas | G01N 35/00871 702/108 |
| 2014/0039954 | A1 * | 2/2014 | Wong | G06Q 10/063118 705/7.17 |

* cited by examiner

TECHNIQUES FOR PROVIDING DATA ACQUISITION INTERFACES FOR ANALYTICAL INSTRUMENTS

CROSS-REFERENCE TO RELATED APPLICATIONS

This application claims the benefit of and priority to U.S. Provisional Patent Application No. 62/842,168, filed on May 2, 2019, the entire contents of which are incorporated by reference.

TECHNICAL FIELD

Embodiments herein generally relate to managing analytical instruments, and, more particularly, to processes for interfacing with and acquiring data from analytical instruments.

BACKGROUND

Research and clinical facilities that perform analytical studies, such as a proteomics research group or a toxicology laboratory, typically rely on a wide range of instruments to acquire data. Even for a particular type of instrument, such as a mass spectrometer (MS) for proteomics research, a facility may have different instruments with particular strengths and weaknesses for a certain experiment. Such instruments may be provided by different manufacturers and/or controlled via different control system hardware and/or software. In addition, instrument data output (for instance, raw or native data) is usually subjected to processing via proprietary applications provided by the instrument manufacturer. As a result, analytical facilities generally operate with a group of instruments that produce different results for the same analysis and/or are not able to effectively interact and share data. Accordingly, although the proliferation of different instruments allows for flexibility and choice in carrying out analyses, researchers are not able to meaningfully and seamlessly acquire and process data across the population of analytical devices in their facilities. In addition, operators are continually required to learn different ways to perform the same functions on different instruments.

DETAILED DESCRIPTION

Figure 1:
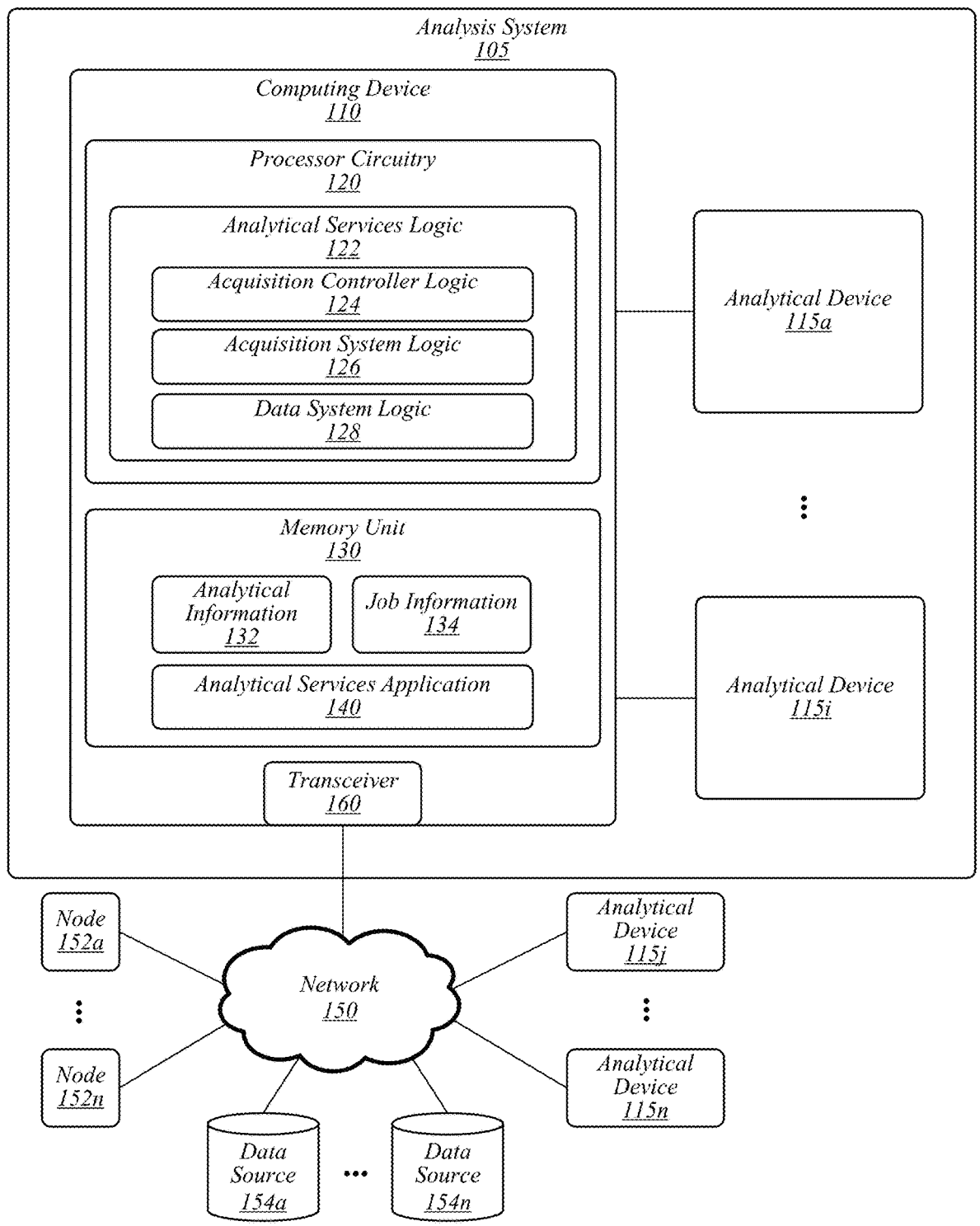
FIG. 1 illustrates an embodiment of a first operating environment.

Various embodiments may generally be directed toward systems, methods, and/or apparatus for processing data generated by analytical instruments. In some embodiments, an acquisition platform may be operative to provide an interface configured to perform acquisition processes to receive, process, store, and/or otherwise manage analytical data generated by one or more instrument systems. In exemplary embodiments, the acquisition platform may provide for, among other things, instrument control at the instrument level to facilitate data system interactions with instrument systems and components such as methods, reports, and raw data.

The acquisition platform may include various components, such as acquisition controllers, acquisition systems, acquisition adapters, and/or acquisition interfaces configured according to an acquisition specification. In some embodiments, an acquisition interface may be configured to manage a plurality of acquisition systems, each associated with a data system. In various embodiments, an acquisition controller may be an instance or implementation of the acquisition interface. In exemplary embodiments, a data system may be operative to manage at least one analytical instrument and/or instrument system. In various embodiments, each acquisition system may receive an execute jobs from an associated data system. An acquisition system may be operative to generate and/or provide job information, such as job status, job data, and/or the like to data consumers, such as a data system.

An acquisition platform according to some embodiments may provide multiple technological advantages over conventional systems, including improvements in computing technology. For example, the acquisition platform may include a set of interfaces and entities that facilitate data system interactions with analytical instruments and/or instrument systems, as well as components such as methods, reports, and raw data. Standard interfaces according to some embodiments may permit a loose coupling between the data system and instrument system while maintaining a high level of interoperability. In one non-limiting technological advantage, separation of the acquisition system from the data system may allow multiple data systems to share a single acquisition controller, for example, on a common network. Such separation may also allow different technologies to integrate seamlessly and, therefore, provide for integrated systems with dedicated controllers. In another non-limiting technological advantage, the acquisition platform may allow for isolation of the analytical instruments or instrument systems from a host data system, allowing a standardized interface to facilitate multiple data system types to use different acquisition controllers.

Conventional analytical systems include proprietary applications tightly coupled with the architecture of the analytical instrument or instrument system, particularly in the area of instrument control. For example, conventional systems include instrument-specific functionality that makes is difficult if not impossible to deliver individual instrument drivers off-cycle from a main data system. Accordingly, in a further non-limiting technological advantage, some embodiments may redefine the conventional instrument data system boundary and treat the instrument system, not as a collection of individual boxes to be managed by the data system itself, but as a holistic unit capable of self-management. Redefining the data system/instrument system boundary according to some embodiments provides many technological advantages over conventional systems. In one illustrative and non-restrictive example, it enables the instrument system itself to be standalone and delivered off cycle from the main data system. In a second illustrative and non-restrictive example, it becomes easier to have a cohesive strategy around remote monitoring and diagnostics of instrument systems particularly, for example, in connection with network-based technologies, such as internet-of-things (IoT) and cloud-based analytics. In a third illustrative and non-restrictive example, it allows for cross platform type development whereby the same acquisition controller may be used in multiple data systems and, alternatively, multiple data systems may use the same acquisition controller.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage analytical information associated with analytical devices 115a-n. In some embodiments, analytical devices 115a-n may be or may include a chromatography system, a liquid chromatography (LC) system, a gas chromatography (GC) system, a mass analyzer system, a mass detector system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, an ultraviolet (UV) detector, a visible light detector, a solid-phase extraction system, a sample preparation system, a sample introduction system, a pump system, a capillary electrophoresis instrument, combinations thereof, components thereof, variations thereof, and/or the like. Although LC, MS, and LC-MS are used in examples in this detailed description, embodiments are not so limited, as other analytical instruments capable of operating according to some embodiments are contemplated herein.

In various embodiments, analytical device 115a-n may be or may include an instrument module. In general, an instrument module may include an individual instrument, such as a solvent manager, sample manager, pump, a single quadrupole MS, and/or the like. In some embodiments, analytical device 115a-n may be or may include an instrument system. In general, an instrument system may include a collection of instrument modules that operate collectively as a holistic unit. For example, an instrument system may include an analytical device (for instance, an LC or MS device) capable of providing analytical data (measurements) and supporting components (for example, an injector, detector, pump, control systems, and/or the like for an LC or MS system) that facilitate the generation of the analytical data by the analytical device. Embodiments are not limited in this context.

In some embodiments, analytical device 115a-n may operate to perform an analysis and generate analytical information 132. In various embodiments, analytical information 132 may include information, data, files, charts, graphs, images, and/or the like generated by an analytical instrument as a result of performing an analysis method. For example, for an LC-MS system, analytical device 115a-n may separate a sample and perform mass analysis on the separated sample according to a specified method to generate analytical information 132 that may include raw, native, or otherwise unprocessed data, chromatograms, spectra, peak lists, mass values, retention time values, concentration values, compound identification information, and/or the like. In various embodiments, analytical information 132 may include information resulting from a quality control process, such as a system suitability test, quality control check, and/or the like.

In various embodiments, analysis system 105 may include computing device 110 communicatively coupled to analytical device 115a-n or otherwise configured to receive and store analytical information 132 associated with analytical device 115. For example, analytical device 115a-n may operate to provide analytical information 132 directly to computing device 110 and/or to a location on a network 150 (for instance, a cloud computing environment) accessible to computing device 110. In some embodiments, computing device 110 may be operative to control, monitor, manage, or otherwise process various operational functions of analytical device 115a-n. In some embodiments, computing device 110 may be operative to provide analytical information 132 to a location on a network 150 through a secure or authenticated connection. In some embodiments, computing device 110 may be or may include a stand-alone computing device, such as a personal computer (PC), server, tablet computing device, cloud computing device, mobile computing device (for instance, a smart phone, tablet computing device, and/or the like), data appliance, and/or the like. In various embodiments, computing device 110 may be or may include a controller or control system integrated into analytical device 115a-n to control operational aspects thereof.

Although only one computing device 110 is depicted in FIG. 1, embodiments are not so limited. In various embodiments, the functions, operations, configurations, data storage functions, applications, logic, and/or the like described with respect to computing device 110 may be performed by and/or stored in one or more other computing devices. A single computing device 110 is depicted for illustrative purposes only to simplify the figure.

As shown in FIG. 1, computing device 110 may include processor circuitry 120, a memory unit 130, and a transceiver 160. Processor circuitry 120 may be communicatively coupled to memory unit 130 and/or transceiver 160.

Processor circuitry 120 may include and/or may access various logic for performing processes according to some embodiments. For instance, processor circuitry 120 may include and/or may access analytical services logic 122, acquisition controller logic 124, acquisition system logic 126, and/or data system logic 128. Processing circuitry 120 and/or analytical services logic 122, acquisition controller logic 124, acquisition system logic 126, and/or data system logic 128, and/or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by the exemplary computing architecture 800. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although analytical services logic 122 is depicted in FIG. 1 as being within processor circuitry 120, embodiments are not so limited. In addition, although acquisition controller logic 124, acquisition system logic 126, and data system logic 128 are depicted as being a logic of analytical services logic 122, embodiments are not so limited, as acquisition controller logic 124, data system logic 128, and/or system controller logic may be separate logics and/or may not be standalone logics but, rather, a part of analytical services logic 122. For example, analytical services logic 122, and/or any component thereof, may be located within an accelerator, a processor core, an interface, an individual processor die, implemented entirely as a software application (for instance, analytical services application 140) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store an analytical services application 140 that may operate, alone or in combination with analytical services logic 122, to perform various analytical functions according to some embodiments. In various embodiments, analytical services application 140 may interact with analytical devices 115*a-n* and/or components thereof through various drivers (which may include application programming interfaces (APIs) and/or the like), software and/or hardware interfaces, and/or the like.

In various embodiments, analytical services logic 122 may be configured to provide and/or implement analytical services for analytical devices 115*a-n*. In general, analytical services may include processes for managing analytical devices, including facilitating execution of jobs on analytical devices and acquiring data from analytical devices. In some embodiments, a job may be or may include operations to perform an analytical method using an instrument system (for instance, a method may execute to perform multiple jobs). In other embodiments, a job may include methods and/or executing different methods (for instance, a job may include executing one or more methods).

In exemplary embodiments, analytical services logic 122 may be configured as an interface specification for analytical devices, for example, to facilitate acquisition controllers, acquisition adapters, acquisition systems, and/or data systems according to some embodiments. Analytical services logic 122 may enable control of analytical devices 115*a-n* at the component (or instrument) level. In various embodiments, analytical services logic 122 may operate to provide device-agnostic interfaces that allow different components (such as acquisition controllers, data systems, analytical devices, and/or the like) to interact, perform jobs (for instance, jobs to perform analytical methods), and acquire data.

In various embodiments, analytical services logic 122 may include various logics, such as acquisition controller logic 124, acquisition system logic 126, and/or data system logic 128, to provide analytical services. In some embodiments, acquisition controller logic 124 may operate to implement an acquisition controller on computing device 110 (see, for example, acquisition controller elements depicted in FIGS. 2-6). In various embodiments, acquisition controller logic 124 may be configured to register with one or more data systems, for example, to accept and execute jobs for the data system. In various embodiments, acquisition controller logic 124 may operate to generate an acquisition system, for instance executed by acquisition system logic 126. Analytical devices 115*a-n* and/or elements thereof may be designated as resources or modules. In exemplary embodiments, an acquisition system may be defined as a logical or discrete group of instrument resources or modules that are connected to an acquisition controller to perform a function.

Acquisition system logic 126 may operate to implement an acquisition system created by an acquisition controller. In various embodiments, an acquisition system may be configured to accept jobs (for instance, "acquisition jobs") from a data system via an acquisition controller. A job may include a set of tasks to be performed on an instrument system to carry out an analysis method. For example, in an MS or LC-MS system, a job may include submission of a batch of samples, system equilibration, and/or a sample injection and the tasks may include the individual tasks or steps required to perform the submission of the batch of samples, system equilibration, and/or injection on the instrument. An acquisition system may operate to execute the job (or, more specifically, facilitate the execution of the job by the corresponding instrument system) and to provide status information to certain data consumers, such as the data system that submitted the job to the acquisition controller.

Data system logic 128 may operate to implement a data system on computing device 110 (see, for example, data system elements depicted in FIGS. 2-6). In some embodiments, a data system may be configured to register with an acquisition controller. A data system may operate to submit jobs to an acquisition controller for execution via an analytical device 115*a-n* (for instance, via an acquisition controller). In various embodiments, a data system may be operably coupled to an analytical device 115*a-n* and a computing device implementing an acquisition controller (see, for example, FIG. 2). In some embodiments, an acquisition controller and corresponding acquisition systems may be independent of any one particular data system and, in some instance, may be shared by multiple data systems. In exemplary embodiments, a data system may operate to provide functionality to allow an operator to generate and/or execute jobs (for instance, jobs to perform analytical methods) and to collect data generated as a result of the jobs. Accordingly, in some embodiments, a data system may interact with acquisition controllers to use acquisition systems to execute analytical jobs and generate analytical data sets. Non-limiting examples of data systems may include computing systems operating the UNIFI® platform and/or the Empower® platform provided by Waters Corporation of Milford, Mass., United States.

In some embodiments, memory unit 130 may store analytical information 132, job information 134, and/or other information. In various embodiments, analytical information 132 may include information relating to analytical devices 115*a-n* and/or analytical methods performed via analytical devices 115-*an*. For example, analytical information 132 may include, without limitation, analytical methods, analytical data, unprocessed, raw, and/or native data, plots, charts, graphs, channel data, and/or the like generated before, during, or after the performance of an analytical method by an analytical device 115*a-n*. In some embodiments, job information 134 may include information associated with jobs being executed or implemented via a component of analysis system. Non-limiting examples of job information 134 may include, tasks, task lists, task queues, jobs, job lists, job queues, job submission information (for instance, submitting data system and/or the like), job status, task status, job events, task events, and/or the like. Embodiments are not limited in this context.

Figure 2:
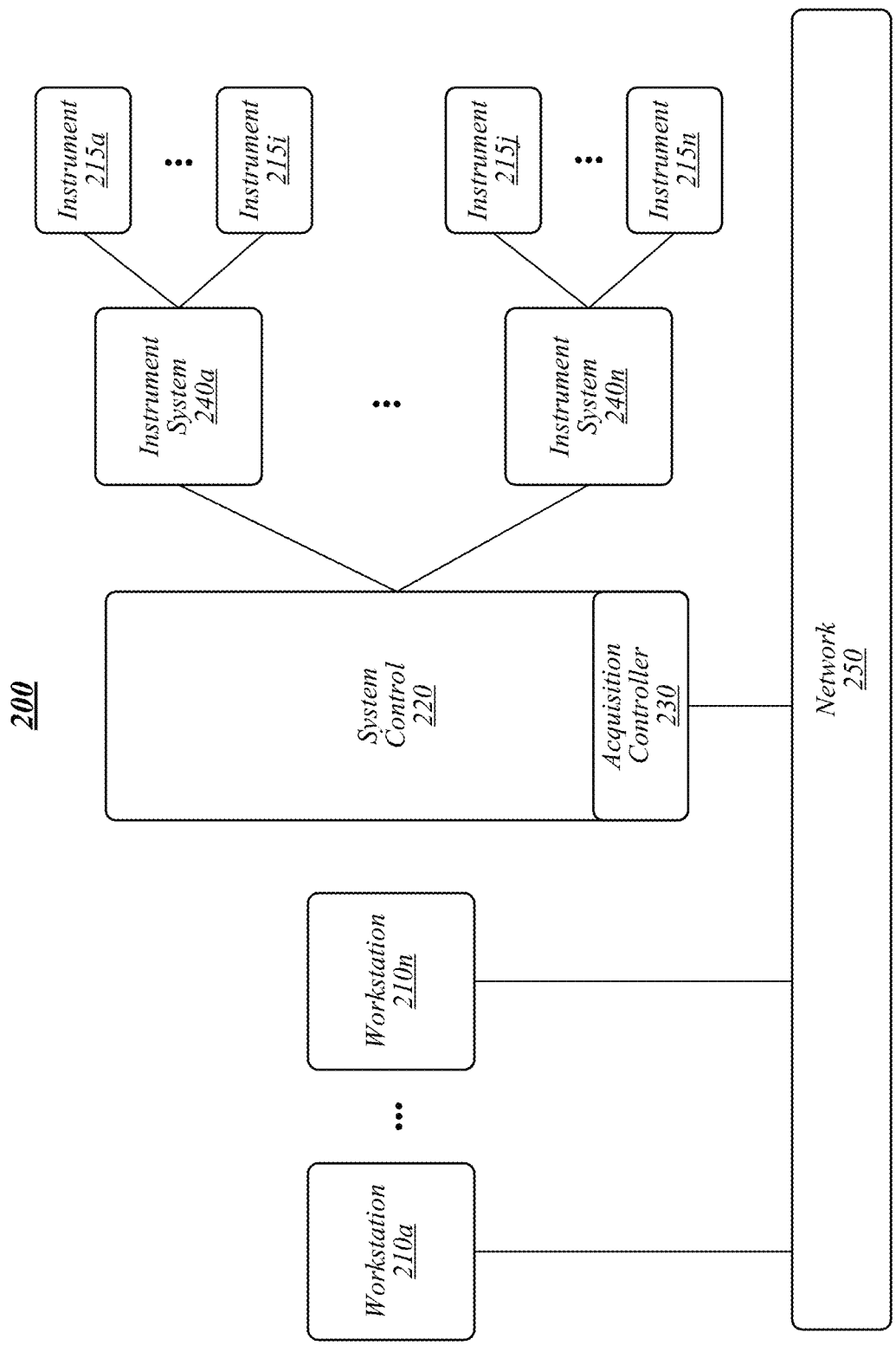
FIG. 2 illustrates an embodiment of a second operating environment.

FIG. 2 illustrates an example of an operating environment 200 that may be representative of some embodiments. Operating environment 200, for example, may include a configuration of analysis system 105 components in an enterprise and/or clinical environment. As shown in FIG. 2, operating environment 200 may include a network 250 operative to communicatively couple elements of operating environment 200, such as workstations 210*a-n*, system control 220, and/or the like.

In various embodiments, instrument systems 240*a-n* may be operably coupled to instruments 215*a-n*. For example, instrument system 240*a* may be operably coupled to instrument 215*a* that is or includes an LC-MS instrument system. In another example, instrument system 240-*n* may be operably coupled to instrument 215*j* that is or includes an IMS system, and may be operably coupled to instrument 215*n* that includes a UV detector. Embodiments are not limited in this context.

In exemplary embodiments, instrument systems 240*a-n* may be operably coupled to system control 220, such as a laboratory network device (LND) or an integrated instrument system (for instance, an integrated LC-MS system). In some embodiments, system control 220 may be configured to execute an acquisition controller 230. In various embodiments, jobs may be submitted via network 250 to acquisition controller 230 to be executed by system control 220.

In some embodiments, workstations 210*a-n* may be connected to network 250. In various embodiments, workstations 210*a-n* may operate as a presentation layer for operating environment 200. In some embodiments, workstations 210*a-n* may operate as an acquisition system console (or "console") for interacting with system control 220, instrument systems 240*a-n*, and/or instruments 215*a-n*. A console may provide user access to configuration, diagnostics, maintenance, status, control, and/or the like for components of operating environment 200. Embodiments are not limited in this context.

Figure 3:
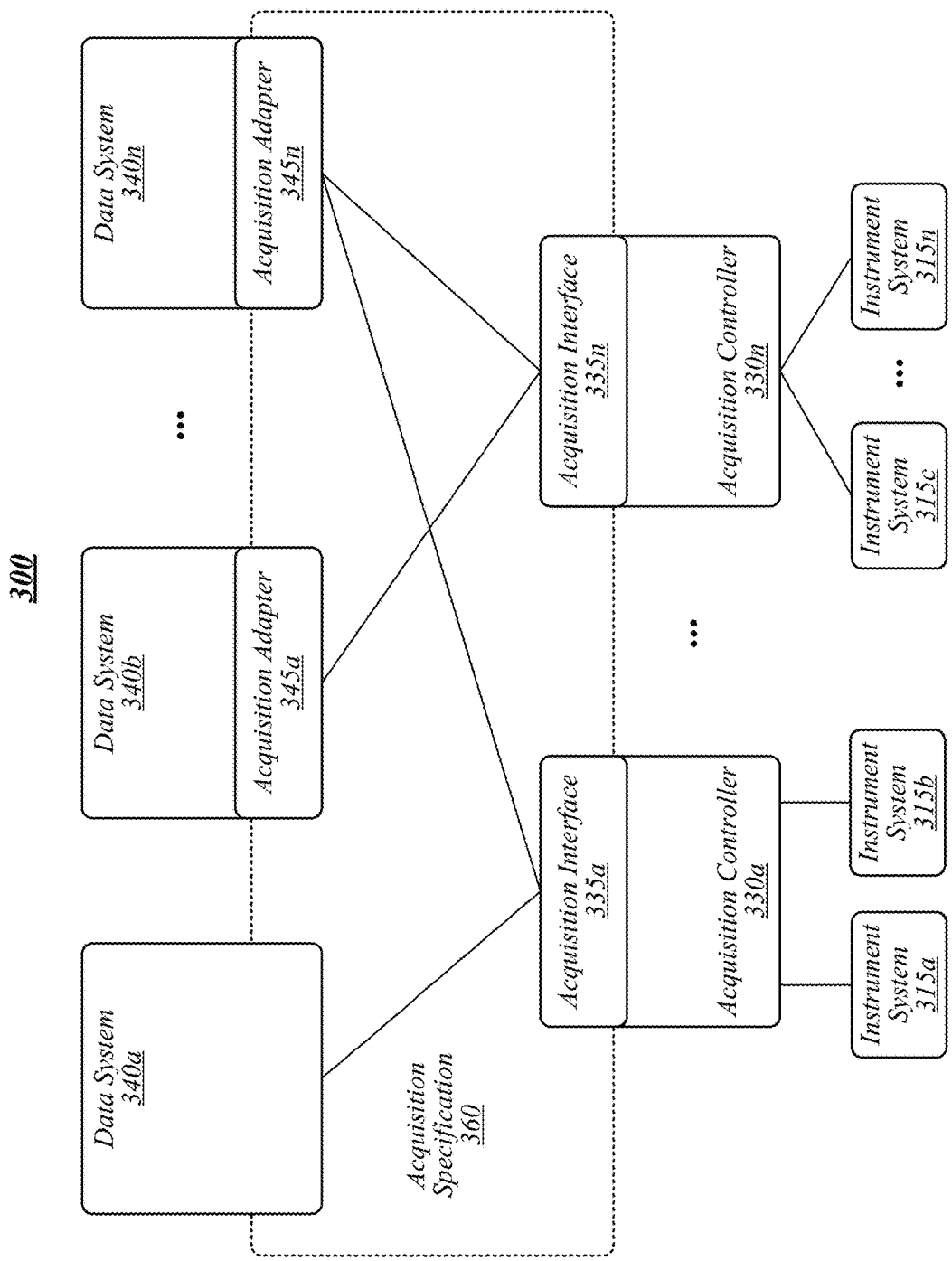
FIG. 3 illustrates an embodiment of a third operating environment.

FIG. 3 illustrates an example of an operating environment 300 that may be representative of some embodiments. As shown in FIG. 3, operating environment 300 may include data systems 340*a-n* operably coupled to acquisition controllers 330*a-n*. In some embodiments, data systems 340*a-n* may submit jobs to acquisition controllers 330*a-n*, for example, via an acquisition adapter 345*a-n*. Acquisition specification 360 may be or may include a specification required for components of operating environment 300 to interact with each other to perform analytical processes according to some embodiments. For example, acquisition specification 360 may include a set of software and/or hardware constructs that may be implemented to provide interfaces, such as application programming interfaces (APIs), drivers, communication ports, and/or the like between compliant data systems 340*a-n* and compliant acquisition controllers 330*a-n* to facilitate operation of instrument systems 315*a-n*. Accordingly, acquisition specification 360 may be operate as a "contract" between components of operating environment 300, such as instrument systems 315*a-n*, acquisition controllers 330*a-n*, and/or data systems 340*a-n*.

Accordingly, acquisition controllers 330*a-n* may be data system and/or platform independent as long as the components are operating, at least partially, according to acquisition specification 360. In various embodiments, each acquisition controller 330*a-n* may be independent of one another and may co-exist on a common network. In exemplary embodiments, each acquisition controller 330*a-n* may be data system independent and may receive and implement job requests from multiple data systems 340*a-n* and multiple types of data systems 340*a-n*.

Components, applications, and/or the like may communicate with each other within operating environment 300 and submit and receive information, jobs, etc., by implementing constructs, such as APIs, according to acquisition specification 360. In this manner, acquisition controller 330*a-n* may be agnostic to the type or manufacturer of instrument system 315*a-n*, data system 340*a-n*, and/or the like. For example, if the instrument system 315*a-n*, data system 340*a-n*, and/or the like implements acquisition specification 360, acquisition controller 330*a-n* may be able to communicate with instrument system 315*a-n*, data system 340*a-n*, and/or the like and facilitate the performance of jobs, for instance, analytical methods run on instrument systems 315*a-n*.

In some embodiments, acquisition controller 330*a-n* may include an acquisition interface 335*a-n* operative to facilitate communication between acquisition controller 330*a-n* and data system 340*a-n* configured according to acquisition specification 360. In various embodiments, acquisition interface 335*a-n* may include APIs that may be called from data systems 340*a-n* to implement processes according to some embodiments, such as the submission of jobs, status requests, and/or the like. In some embodiments, acquisition controller 330*a-n* may operate to implement acquisition specification 360, for instance, operating as an acquisition specification "server." In some embodiments, acquisition jobs and the resulting job statuses, job events, and job data are the artifacts that flow across the interface boundary between data systems 340 and acquisition controllers 330.

In various embodiments, instrument systems 315*a*-*n*, data systems 340*a*-*n*, acquisition interfaces 335*a*-*n*, and/or acquisition controllers 330*a*-*n* may be operative to communicate using various known protocols and/or variations thereof, including, without limitation, transmission control protocol/internet protocol (TCP/IP), HyperText Transfer Protocol (HTTP), HyperText Transfer Protocol Secure (HTTPS), Ethernet, Wi-Fi, serial communication protocols, versions thereof, extensions thereof, combinations thereof, and/or the like. In some embodiments, communication within and between elements of operating environment may be at least partially facilitated via HTTP and/or HTTPS over TCP/IP. Embodiments are not limited in this context.

In various embodiments, data systems 340*a*-*n* may implement an acquisition adapter 345*a*-*n*. In some embodiments, an acquisition adapter 345*a*-*n* may be a logic construct operative to allow a legacy system or other system not initially configured according to acquisition specification 360 to operate with acquisition controller according to acquisition specification 360. In this manner, acquisition controller 330*a*-*n* may work with any data system that includes a compatible acquisition adapter 345*a*-*n*.

In various embodiments, acquisition controller 330*a*-*n* may be or may be executed on an individual computing device. In other embodiments, acquisition controller 330*a*-*n* may be executed or embedded in another computing device, such as data system 340*a*-*n* and/or instrument system 315*a*-*n*. In exemplary embodiments, data system 340*a*-*n* may include or may be executed on an individual computing device. In other embodiments, data system 340*a*-*n* may be executed or embedded in another computing device, such as instrument system 315*a*-*n*. Embodiments are not limited in this context.

Figure 4:
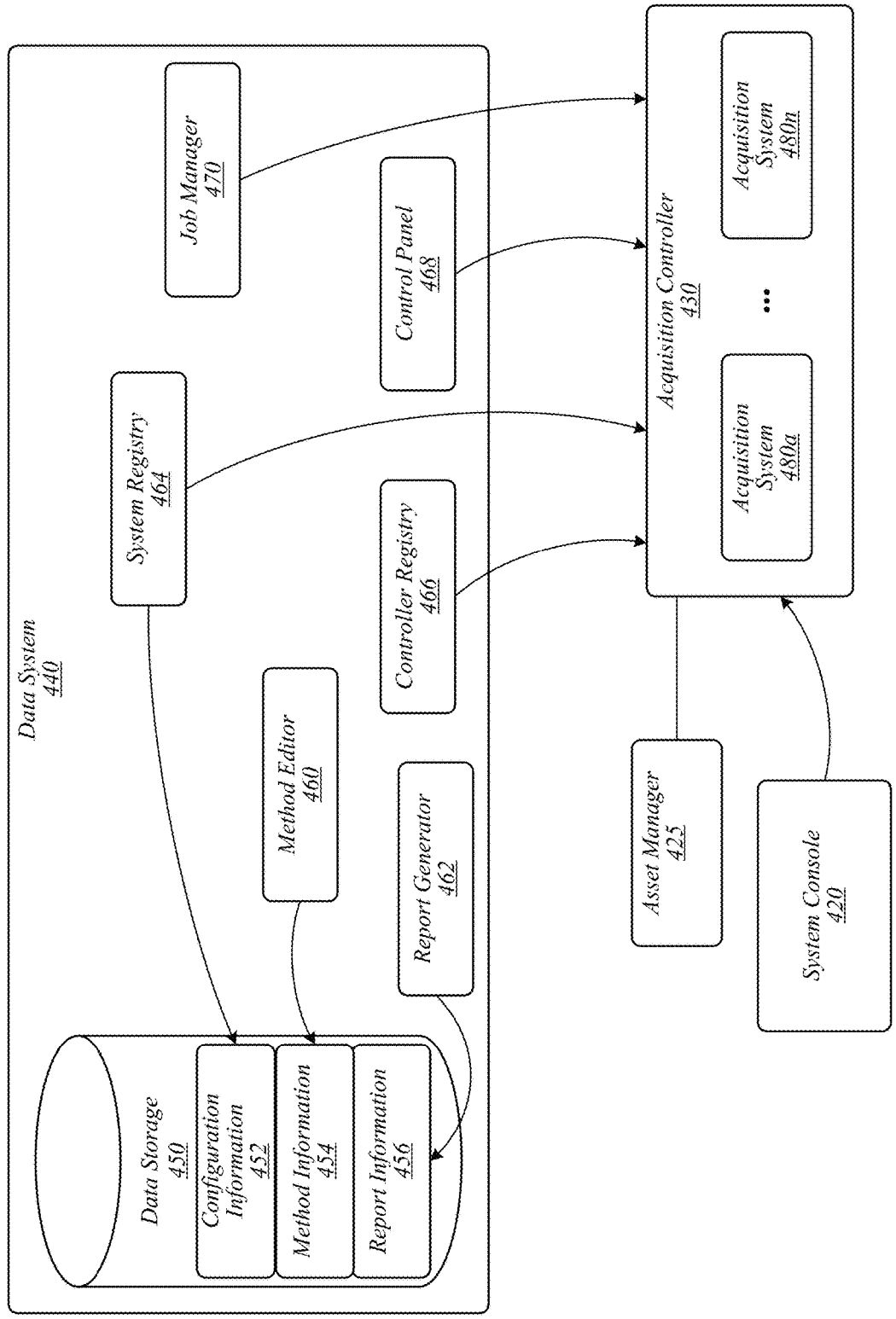
FIG. 4 illustrates an embodiment of a fourth operating environment.

FIG. 4 illustrates an example of an operating environment 400 that may be representative of some embodiments. As shown in FIG. 4, operating environment 400 may include acquisition controller 430 and data system 440. In some embodiments, acquisition controller 430 may implement an acquisition specification to integrate with the operational expectations of data system 440 (for instance, to communicate via APIs). In various embodiments, acquisition controller 430 may generate, administrate, and/or manage acquisition systems 480*a*-*n* operating therein. In some embodiments, each acquisition system 480*a*-*n* may include instrument resources. For example, each acquisition system 480*a*-*n* may include a set, group, collection, or other specification of instrument resources that are connected to or otherwise accessible to acquisition controller. In some embodiments, an acquisition system 480*a*-*n* may include all or some of the components to perform an analytical method and/or components thereof, such as a job or task associated with the analytical method. In a first example, in an LC-MS system, a first acquisition system 480*a*-*n* to prepare a sample, a second acquisition system 480*a*-*n* to perform a first phase of liquid chromatography, a third acquisition system 480*a*-*n* to perform a second phase of liquid chromatography, a fourth acquisition system 480*a*-*n* to perform mass spectrometry on the separated sample, and a fifth acquisition system 480*a*-*n* for the software platform operating the MS. In a second example, in an LC-MS system, one acquisition system 480*a*-*n* may be used for all or substantially all of the components of the LC-MS system. In general, an acquisition system 480*a*-*n* may be configured to include any number of system resources. In some embodiments, an acquisition system 480*a*-*n* may be configured to include system resources according manual input, automatic acquisition system generation (for instance, according to the acquisition specification, manufacturer recommendations, analytical method, the type of resources, and/or the like), and/or combinations thereof.

Acquisition controller 430 may register with data system 440 to allow data system 440 to begin communicating with acquisition controller. For example, data system 440 may include a system registry service 464 to register one or more acquisition controllers 430. In an illustrative embodiment, registration may include system discovery via HTTP endpoint and establishment of a relationship (for instance, a secure or trust relationship) between data system 440 and acquisition system 430. In some embodiments, information associated with acquisition controller 430, acquisition services 480*a*-*n*, and/or the like may be stored in data system 440 within data storage, for instance, as configuration information 452. In addition, each acquisition system 480*a*-*n* associated with data system 440 may be registered by data system 440, for instance, via system registry 464.

In some embodiments, acquisition systems 480*a*-*n* may operate to receive jobs from a data system 440. In some embodiments, a job may include an operation performed to carry out an analytical method. In various embodiments, a job may be or may include an analysis or batch of analyses to be performed by an analytical instrument. In exemplary embodiments, a job may include a batch of tasks, with each task being an operation that may be performed by a system, such as an LC-MS system. In some embodiments, a job may include one or more tasks, which may include a high-level function of a system. A non-limiting example of a task for an LC-MS system may include, without limitation, an injection, equilibration, and/or the like. For example, a task in an LC-MS system may be or may include functions including, without limitation, accessing a sample, separating a sample, injecting a sample, introducing a sample into an instrument, checking quality control pass/fail, processing data, and/or the like. Each job may include one or more tasks that are required to be performed to execute the job. For example, an injection job in an MS system may include the tasks or activities of obtaining the sample within the injector device (for instance, selecting the appropriate sample from a sample tray), injecting the sample in the MS instrument, and cleaning the injector. In various embodiments, jobs may be added to a job queue within an acquisition system 480*a*-*n*. Jobs may be de-queued and executed according to the job queue logic.

Acquisition systems 480*a*-*n* may receive data generated during execution of a job and/or task of the job. The data may ultimately be transmitted to data system 440. In exemplary embodiments, acquisition systems 480*a*-*n* may buffer collected job data locally, for example, until transmission of the data to data system 440 is complete and/or verified.

In various embodiments, acquisition systems 480*a*-*n* may provide a real-time indication of the data being generated by the system. For example, real-time data may be displayed, for example, in the form of a plot or graph within the data system via data system 440 and/or system console 420. In some embodiments, acquisition systems 480*a*-*n* may notify data system 440 which submitted a job of all milestone events that occur during the execution of the job. In some embodiments, acquisition systems 480*a*-*n* may notify data system 440 which submitted a job of all informational events directed to the owner of the job. In various embodiments, acquisition systems 480*a*-*n* may provide the status of a job so that a user has an indication of the current state of job activity. In exemplary embodiments, acquisition systems 480*a*-*n* may provide system status so that the user has an indication of the current state of the system.

In some embodiments, system console 420 may provide a user interface for interacting with components of operating environment 400, such as data system 440, acquisition controller 430, and/or instrument systems (not shown). For example, in various embodiments, an acquisition system 480a-n may provide an HTTP endpoint exposing a user interface accessible via system console 420. In exemplary embodiments, system console 420 may be used for control and/or accessing data, such as setting parameters, initiating methods, viewing status, viewing analytical data (including real-time and/or historical data), viewing system messages, system diagnostic functions, system maintenance functions, and/or the like. In some embodiments, data system 440 may provide for interaction with acquisition controller 430 and/or components thereof via a user interface implemented by a control panel 468. In various embodiments, operating environment 400 may include an asset manager 425 to manage certain aspects of acquisition controller. In some embodiments, asset manager 425 may be, for example, operatively coupled to acquisition controller 430. In some embodiments, asset manager 425 may operate to manage various administrative aspects of acquisition controller 430, such as software updates, asset (i.e., hardware and/or software asset) management, and/or the like.

Data system 440 may operate to use acquisition controller 430 (and acquisition systems 480a-n thereof) to execute jobs (analytical methods) to generate analytical data sets. In exemplary embodiments, data system 440 may include a method editor service 460 to create and edit methods that may, for example, be used in submitted jobs. Methods may be stored as method information 454 in data storage 450. In other embodiments, data system 440 may access methods from a remote location, such as a database accessible via a network. In various embodiments, a job manager service 470 may be used by data system 440 to create and submit jobs to acquisition controller 430. In some embodiments, data system 440 may include a report generator 462 to generate and/or provide access to reports that may include report information 456 associated with completed or active jobs.

In various embodiments, data system 440 may include a controller registry service 466 to register with and keep a record of each acquisition controller 430 and acquisition system 480a-n data system 440 may access.

In some embodiments, controller registry service 466 may include and/or access a repository that contains an entry for every acquisition controller 430 and/or acquisition service 480a-n data system 440 may access and can communicate with. In various embodiments, the controller registry service 466 may maintain the connection information and security settings that are used to communicate with each acquisition controller 430 and/or acquisition service 480a-n.

Figure 5:
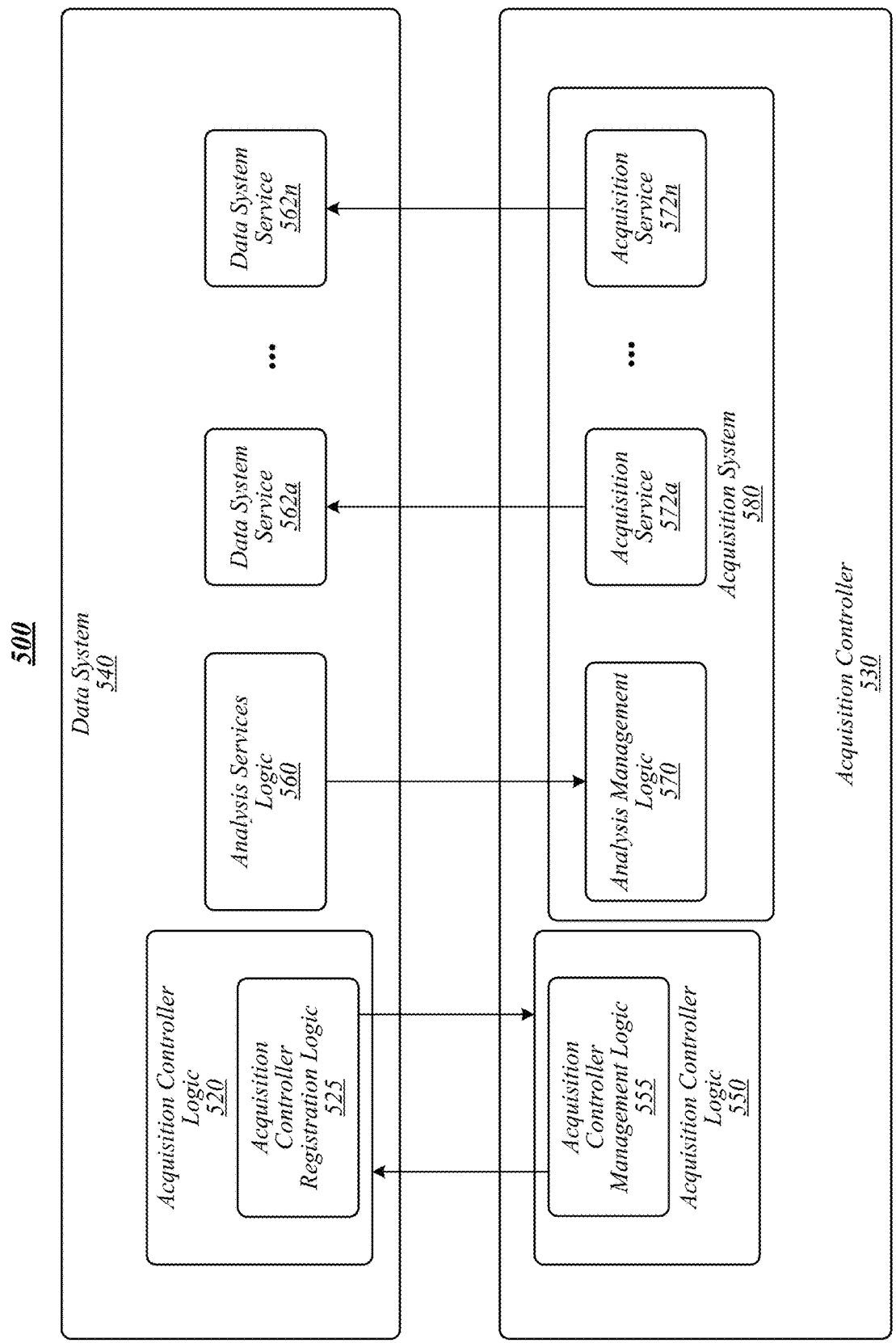
FIG. 5 illustrates an embodiment of a fifth operating environment.

FIG. 5 illustrates an example of an operating environment 500 that may be representative of some embodiments. As shown in FIG. 5, operating environment 500 may include acquisition controller 530 and data system 540. Acquisition controller 530 may include acquisition controller logic 550, acquisition controller management logic 555, acquisition service 580, analysis management logic 570, and acquisition services 572a-n. Data system 540 may include acquisition controller logic 520, acquisition controller registration logic 525, analysis services logic 560, and data system services 562a-n.

In various embodiments, acquisition controller logic 550 may include a set of access points for the management of acquisition controller 530 and components thereof, such as acquisition system 580. In some embodiments, acquisition controller logic 550 may operate to create and manage acquisition systems 580 and instrument modules that make up acquisition systems 580. Acquisition controller management logic 555 may allow acquisition controller 530 to logically group instrument modules into an acquisition system. In some embodiments, acquisition controller management logic 555 may provide functionality to create, delete, and/or modify acquisition systems 580 and to administer or otherwise manage acquisition systems 580 and/or instrument modules associated with acquisition systems 580.

In some embodiments, acquisition controller logic 520 may operate to facilitate communication between data system 540 and acquisition controller 530. For example, acquisition controller registration logic 525 may operate to register acquisition controller 530 and/or acquisition system 580 by data system 540. In various embodiments, acquisition controller logic 520 may operate to authenticate incoming requests, for example, against a list of allowed data systems. For example, communication between acquisition controller 530 and data system 540 may be made over HTTPS with appropriate client certificates.

In various embodiments, data system 540 may include analysis services logic 560 operative to provide sample submission, sample status, and sample plots services. In various embodiments, samples may be submitted or otherwise managed in sample batches. In some embodiments, analysis services logic 560 may provide for control, monitoring, data streaming, and/or the like of submitted samples. Analysis services logic 560 may operate to interact with jobs on acquisition controller 530. Acquisition system 580 may include analysis management logic 570 to manage sample analysis of jobs submitted by data system 540. For example, analysis management logic may include job (or sample batch) submission services to provide an access point for submitting and interacting with jobs being executed via acquisition system, job (or sample batch) status services to provide an access point to obtain the status of a job, and/or job (or sample batch) plots services to provide data related to channels that may provide real-time and/or future plot data relating to a job.

Figure 6A:
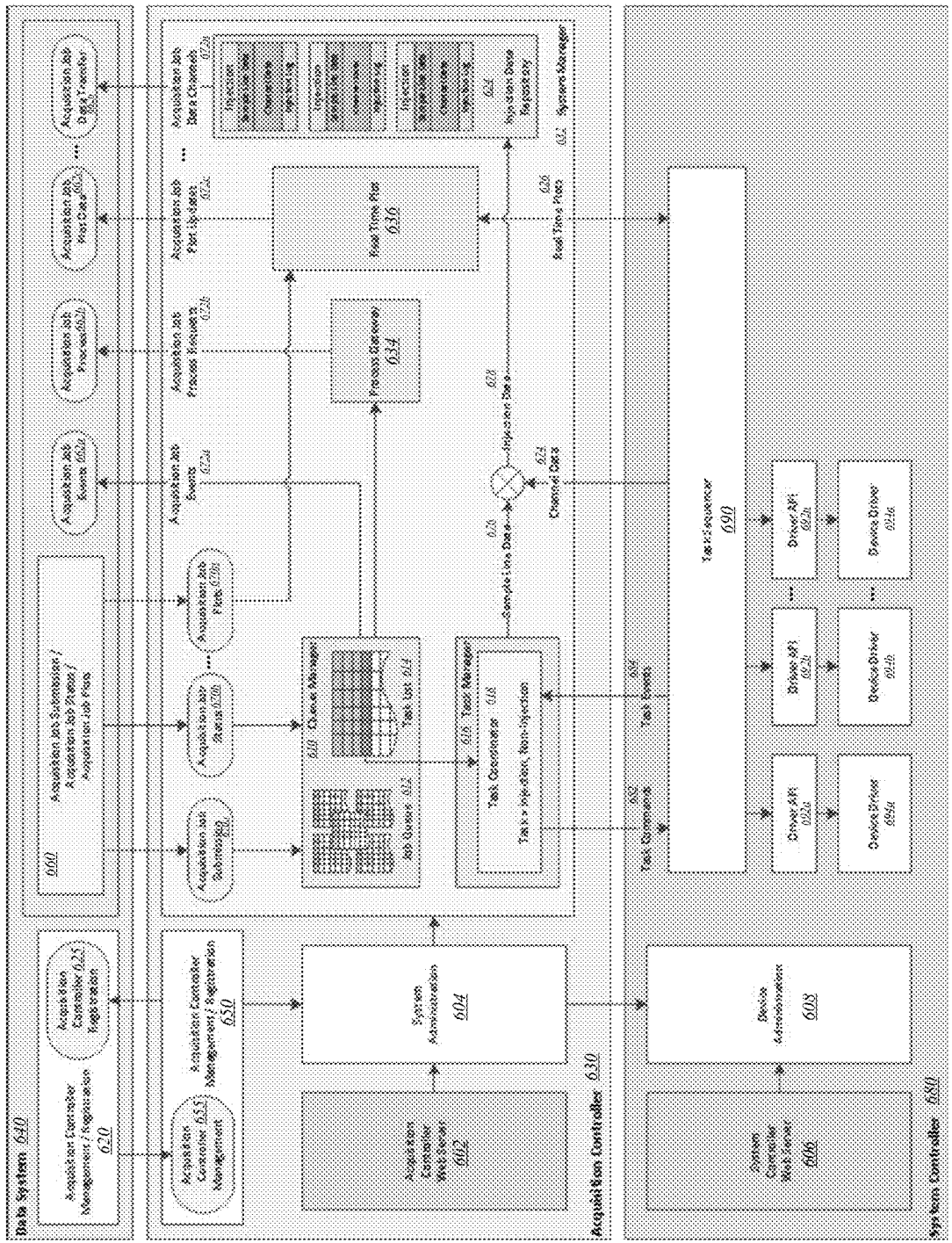
FIG. 6A illustrates an embodiment of a sixth operating environment.

FIG. 6A illustrates an example of an operating environment 600A that may be representative of some embodiments. As shown in FIG. 6A, operating environment 600A may include acquisition controller 630 and data system 640. System manager 632 and system controller 680 may operate to implement an acquisition system according to some embodiments.

In some embodiments, acquisition controller management/registration 620 may operate to facilitate management communication between data system 640 and acquisition controller 630 via acquisition controller management/registration 650. In various embodiments, acquisition controller registration 625 may operate to register acquisition controller 630 and/or acquisition services thereof. Acquisition controller management 655 may provide a set of access points to acquisition controller 630 to data system 640, for instance, for administrative management of acquisition controller 630 and components thereof, the creation and management of acquisition systems, and/or device management of instrument modules of acquisition systems.

In various embodiments, data system 640 may include analysis services logic 660 to manage job submissions, job statuses, and/or job plots for data system 640. In some embodiments, data system 640 may include data system services 662a-n, such as job events 662a, job process requests 662b, job plot data 662c, and/or data transfer 662n. In some embodiments, data system services 662a-n may act as information receivers for specific types of information. Data system services 662a-n may operate to receive (for example, in response to a request) job information, such as events, processes, plot data, analytical data, and/or the like. The job information may be provided to data system services 662a-n via corresponding acquisition services 672a-n. For example, during execution of a job, data system 640 may request job event information, acquisition controller 630 may provide job event information (for instance, via HTTP calls to job events 662a functioning as a job events receiver API) to job events 662a via job events service 672a.

In exemplary embodiments, acquisition controller may include a web server 602 to manage requests, submissions, and/or messages via web interfaces, such as HTTP. In various embodiments, web server 604 may communicate with other components, such as system manager 632 and/or system controller 680 via system administration 604. In some embodiments, all or substantially all communication within operating environment may be via HTTP and/or HTTPS. In various embodiments, at least a portion of communication within operating environment may be via HTTP and/or HTTPS.

Jobs may be submitted by data system 640 via analysis services logic 660 through job submission service 670a. In some embodiments, system manager 632 may include a queue manager 610 operative to receive and enqueue jobs in a job queue 612. In various embodiments, tasks for each job in job queue 612 may be provided as a task list 614 for execution according to the job. In some embodiments, the tasks for each job in job queue 612 may be determined for the job. In another example, a record may be created in task list 614 for each task with a job id field to associate the task with a corresponding job. Jobs may be executed in a sequential order or any other type of order determined by system manager. For example, job queue 612 may be a first-in-first-out (FIFO) queue. In some embodiments, a job list may be provided to visualize a summary of the jobs running or waiting to run on the instrument system. The jobs may be ordered by priority. Jobs at the same priority level are queued in the order that they are submitted. The running job may be the first job on the job queue 612.

Tasks may be submitted to task manager 616 and implemented via a task coordinator 618. In some embodiments, task coordinator 618 may submit task commands 682 to a task sequencer of system controller 680. Task sequencer 690 may interact with driver APIs 692a-n necessary to perform the task, thereby invoking driver APIs 692a-n to communicate with corresponding device drivers 694a-n to cause the instrument modules to operate to perform the task (for instance, turn on/off a pump, introduce a sample into an instrument, process raw data, and/or the like).

In exemplary embodiments, queue manager 610 may provide event information associated with jobs and/or tasks being executed via system manager 632 to job events service 672a. In this manner, job event information may be provided to data system 640 via job events service 662a. In some embodiments, queue manager 610 may provide process information for jobs and/or tasks to a process gateway service 634. Processing information may be provided to job process request service 672b via process gateway service 634. In various embodiments, data system 640 may receive process information via job process service 662b from job process request service 672b of system manager 632.

In some embodiments, real time plot service 636 may operate to receive plot information 626 in real time or substantially real time via task sequencer 690. Analysis services logic 660 may request a job plot via communication with job plots service 670n. In various embodiments, job plots service 670n may provide the request to real time plot service 636, which may provide the plot information to job plot updates service 672c for forwarding to data system 640 via job plot data service 662c.

In exemplary embodiments, system manager 632 may implement a job data channel service 672n. Channel data 674, sample line data 676, and/or injection data 678 may be provided to data repository 624. For example, for injection jobs, data repository 624 may include channel data for each injection, including, without limitation, injection information (for instance, injection identifier), sample line data, channel data, injection log data, and/or the like. The channel data may be provided (for instance, streamed and/or in response to a request) to data system 640 via interaction between job data channels service 672n and job data transfer service 662n.

In various embodiments, data system 640 may submit a request for a job to acquisition controller 630. The job may be enqueued and acquisition controller 630 may send an acknowledgement to data system 640. In some embodiments, acquisition controller 630 may send messages to data system 640 responsive to the job being started, a task of the job being started, task completion, and/or job completion.

In one example, data system 640 may create a job with a number of tasks (for instance, five injections for a separation job on an LC system). Data system 640 may submit the job to acquisition controller 630. In one instance, an acquisition system may be associated with one or more the jobs. For example, the instrument modules to perform the separation job on the LC system may be determined (automatically via acquisition controller 630 logic and/or manually via an operator). In another instance, an acquisition system may already exist and may be automatically selected and/or manually selected to perform the job.

The job is submitted to job queue 612 for later submission (for instance, as specified by an operator, method, instrument conditions, and/or the like) or immediate submission. The job may be broken down into tasks and stored in a task list 614. The tasks may be run through task sequencer 690 to coordinate resources (for instance, instrument systems, devices, modules, components, resources, and/or the like) to run the experiment associated with the job (for instance, auto injector, pumps, sample manager, LC components, MS components, and/or the like necessary to perform the job). The resources of the acquisition service may be generating data artifacts or data channels as the tasks are being executed and/or the resource is being prepared to execute a task. The data artifacts and/or data channels may be sent back to acquisition controller 630 and stored in a local repository, such as injection data repository 624, and tagged with information for the task. In some embodiments, tags may be used to provide metadata associated with a job and/or task. In various embodiments, tags may include user-defined textual elements to pass metadata to acquisition controller 630. The data may be stored in the local repository until acquisition controller 630 can may a connection with the corresponding data transfer endpoint (for instance services 662a-n) of data system 640. Data system 640 may request a status (for instance, job status, plot status, channel status, and/or the like) via analysis services logic 660. In addition, data events and notifications are being generated during execution of each task and may be sent over services 672a-n.

Figure 6B:
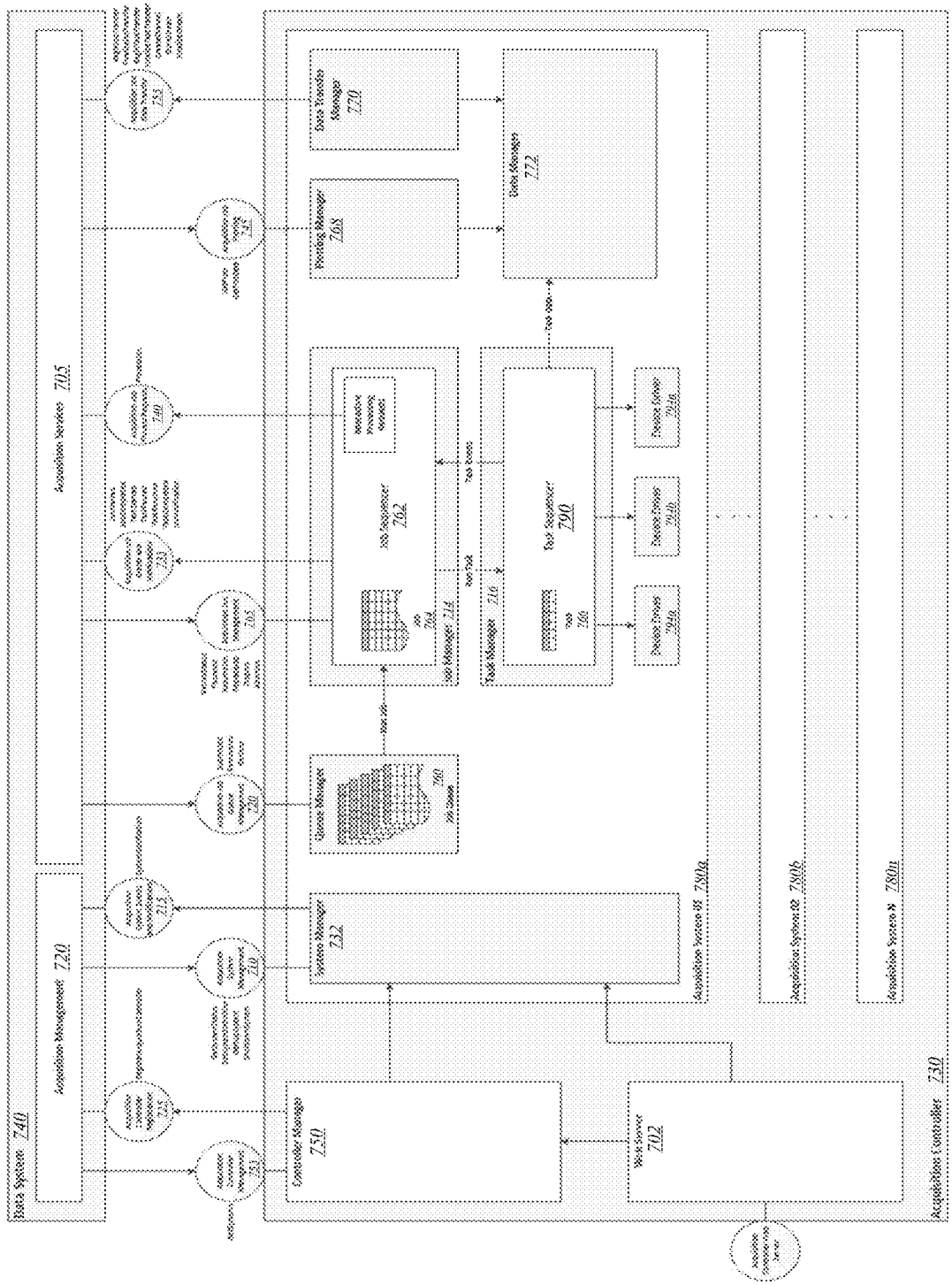
FIG. 6B illustrates an embodiment of a seventh operating environment.

FIG. 6B illustrates an example of an operating environment 600B that may be representative of some embodiments. As shown in FIG. 6B, a data system 740 may include acquisition management 720 and acquisition services 705.

Acquisition management 720 may interact with a controller manager 750 of acquisition controller 730, for instance, with acquisition controller management 755 and/or acquisition controller registration 725 functions. In some embodiments, controller manager 750 may be communicatively coupled to a web server 702.

In various embodiments, acquisition controller 730 may include one or more acquisition systems 780*a-n*. In exemplary embodiments, acquisition system 780*a-n* may include a system manager 732, a queue manager 760, a job manager 714, a task manager 716, a plotting manager 768, a data transfer manager 770, and/or a data manager 772. Acquisition management 720 may interact with system manager 732, for example, with acquisition system management 710 and/or acquisition system events and notifications 715 functions. In exemplary embodiments, acquisition services 705 may interact via one or more acquisition job management 765 functions with a job sequencer 762 of job manager 714. Acquisition services 705 may interact with job manager 714 via an acquisition job events and notifications 735 and acquisition job process requests 740 functions. In some embodiments, job manager 714 may operate to manage the sequencing of a job.

Queue manager 760 may provide a run job instruction to job manager 714 for running a job. Task manager 716 may include a task sequencer 790 to sequence tasks 766. Job manager 714 may operate to provide a run task instruction to task manager 716 (for instance, via task sequencer 790) to run a task. Task manager 716 may operate to manage the sequencing of a task, for example, coordinating devices that make up the system. Task sequencer 790 may notify job sequencer 762 of task events. In some embodiments, task sequencer 790 may interact with device drivers 794*a-n* to facilitate the running of tasks 766. In various embodiments, task sequencer 790 may provide task data to a data manager 772 communicatively coupled to a plotting manager 768 and/or a data transfer manager 770. In some embodiments, plotting manager 768 may interact with acquisition services 705 via an acquisition job plotting function. In various embodiments, data transfer manager 770 may interact with acquisition services 705 via an acquisition job data transfer 765 function.

Figure 7:
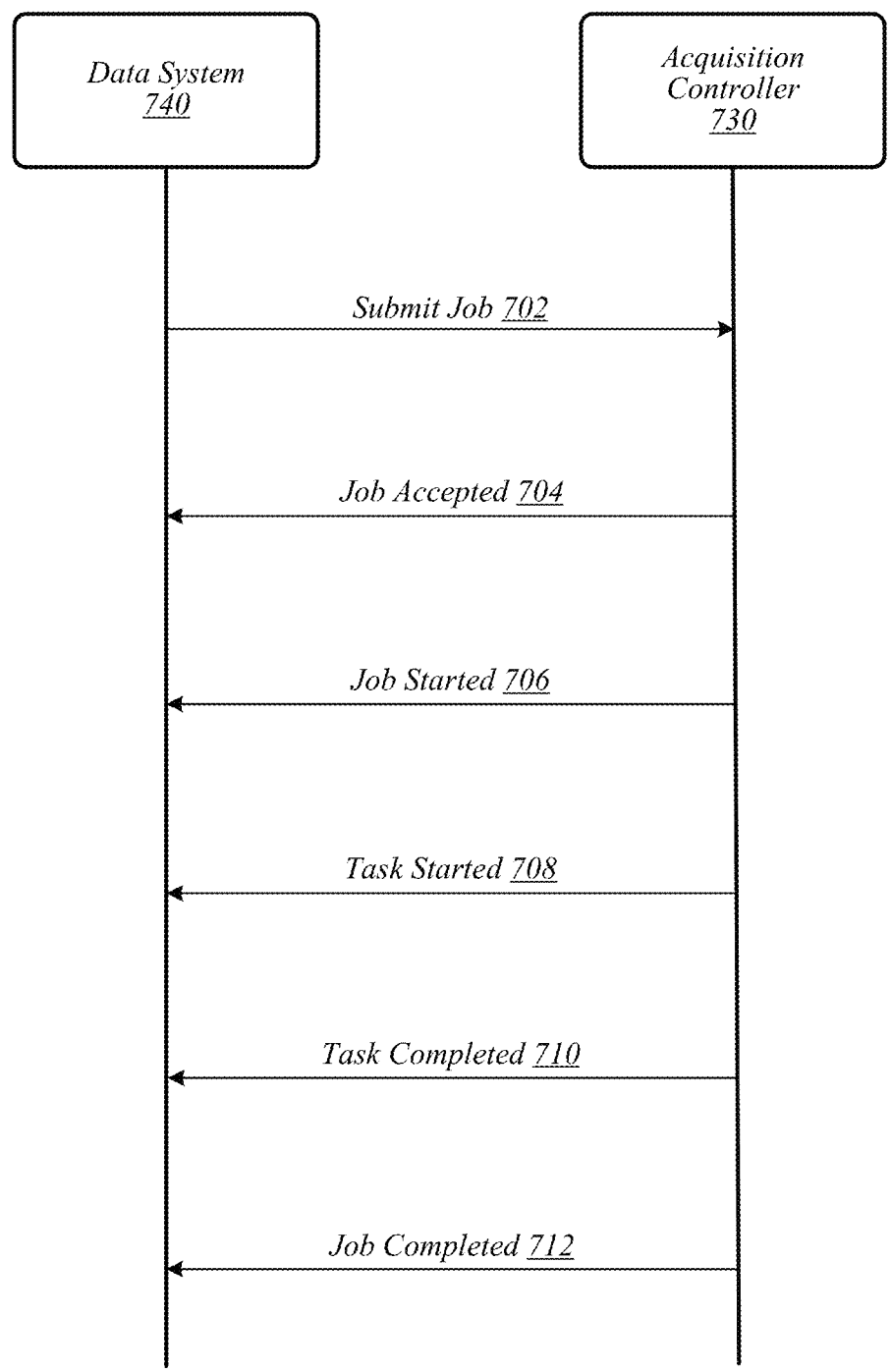
FIG. 7 depicts an illustrative flow sequence for submitting and executing a job according to some embodiments.

FIG. 7 depicts an illustrative flow sequence for submitting and executing a job according to some embodiments. As shown in FIG. 7, data system 740 may submit a job 702 to acquisition controller 730. For example, a job may be defined by data system 740 as an array of tasks having varying types and durations. When a job is executed, the tasks may be executed sequentially or in a non-sequential order, depending on the type and process of the tasks. In some embodiments, each job and/or task may have a reference to a method that specifies instrument settings, parameters, and/or the like to use for the job and/or task. For example, a job may define a single injection from vial A, in a first tray, wrapped by an equilibrate and flush. An intermediate method may be used for specifying the tray or other task details.

Acquisition controller 730 may send a job accepted 704 message to data system 740 responsive to accepting the job. In various embodiments, acquisition controller 730 may perform validation of the job including, for instance, driver validation of individual instrument methods. If the job passes validation, the controller may return job accepted 740 message and/or other messages, such as a created response containing a job model representing the accepted job. If the validation fails, the job is rejected, and bad request error may be returned containing any relevant error details. In various embodiments, a failed job does not exist according to acquisition controller 730 (for instance, it does not receive a job ID or enter the job queue). In some embodiments, an error will be returned if the job queue is full, to indicate that no new jobs can be accepted.

Acquisition controller 730 may send a job started 706 message responsive to starting the job and a task started 708 message responsive to starting a task. In addition, acquisition controller 730 may send a task completed 710 message responsive to completing each task of the job and a job completed 712 message responsive to completing the job.

Figure 8:
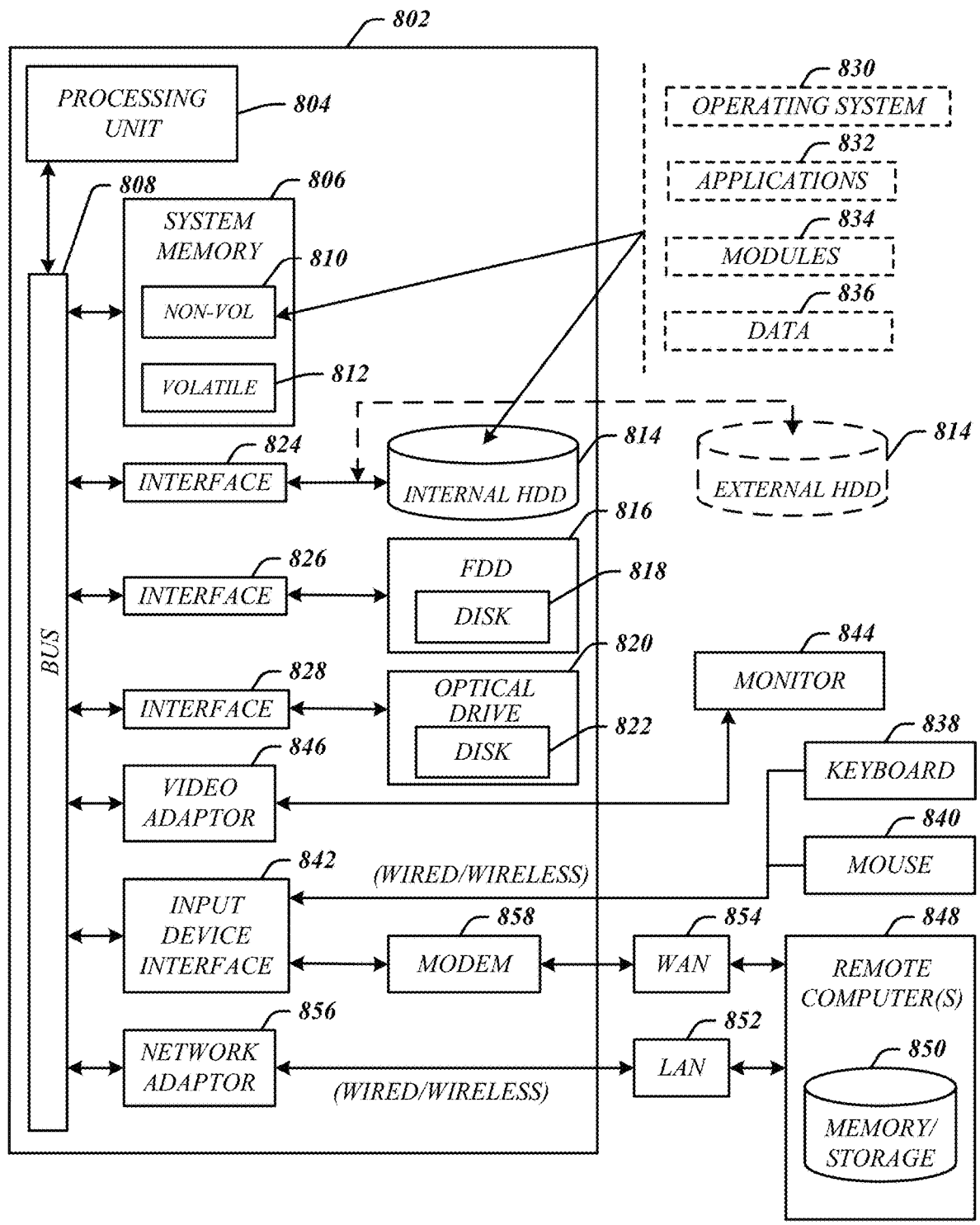
FIG. 8 illustrates an embodiment of a computing architecture.

FIG. 8 illustrates an embodiment of an exemplary computing architecture 800 suitable for implementing various embodiments as previously described. In various embodiments, the computing architecture 800 may comprise or be implemented as part of an electronic device. In some embodiments, the computing architecture 800 may be representative, for example, of computing device 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 800. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806 and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multiprocessor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by a HDD interface 824, an FDD interface 826 and an optical drive interface 828, respectively. The HDD interface 824 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include, for example, the various applications and/or components of computing device 110

A user can enter commands and information into the computer 802 through one or more wire/wireless input devices, for example, a keyboard 838 and a pointing device, such as a mouse 840. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808 but can be connected by other interfaces such as a parallel port, IEEE 1394 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854 or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
   at least one memory; and
   logic, coupled to the at least one memory, operative to implement an acquisition controller shared by a plurality of different types of data systems, each of the plurality of different types of data systems and the acquisition controller implementing an acquisition specification that defines an interface allowing the data systems and acquisition controller to interact, the logic to:
   receive a job request from a data system to perform a job, and
   determine an acquisition system to perform the job, the acquisition system to:
   determine at least one task for the job,
   provide the at least one task to a task sequencer to coordinate performance of the at least one task, and
   provide data artifacts to the data system resulting from performance of the at least one task.

2. The apparatus of claim 1, the logic to generate a new acquisition system to perform the job.

3. The apparatus of claim 1, the acquisition system comprising at least one instrument module.

4. The apparatus of claim 3, the at least one instrument module comprising at least one element of a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, or any combination thereof.

5. The apparatus of claim 1, the job comprising an array of tasks.

6. The apparatus of claim 1, the task comprising an analytical method.

7. The apparatus of claim 1, the logic to:
   validate the job,
   provide an acknowledgement message to the data system responsive to validation of the job, and
   provide an invalid job message to the data system responsive to a determination that the job is invalid.

8. The apparatus of claim 1, the artifacts comprising at least one of job status, job events, job channel data, or job plots.

9. The apparatus of claim 1, the job submitted to a job queue.

10. The apparatus of claim 9, the at least one task stored in a task list for submission to the task sequencer.

11. A method, comprising, via a processor of a computing device executing an acquisition controller:
    receiving a job request from a data system to perform a job; and
    determining an acquisition system to perform the job, the acquisition system shared by a plurality of different types of data systems, each of the plurality of different types of data systems and the acquisition controller implementing an acquisition specification that defines an interface allowing the data systems and acquisition controller to interact, the acquisition system configured to:
    determine at least one task for the job,
    provide the at least one task to a task sequencer to coordinate performance of the at least one task, and
    provide data artifacts to the data system resulting from performance of the at least one task.

12. The method of claim 11, comprising generating a new acquisition system to perform the job.

13. The method of claim 11, the acquisition system comprising at least one instrument module.

14. The method of claim 13, the at least one instrument module comprising at least one element of a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, or any combination thereof.

15. The method of claim 11, the job comprising an array of tasks.

16. The method of claim 11, the task comprising an analytical method.

17. The method of claim 11, comprising:
validating the job;
providing an acknowledgement message to the data system responsive to validation of the job; and
providing an invalid job message to the data system responsive to a determination that the job is invalid.

18. The method of claim 11, the artifacts comprising at least one of job status, job events, job channel data, or job plots.

19. The method of claim 11, the job submitted to a job queue.

20. The method of claim 19, the at least one task stored in a task list for submission to the task sequencer.

* * * * *